United States Patent [19]

Kawai et al.

[11] Patent Number: 5,134,139
[45] Date of Patent: Jul. 28, 1992

[54] 1,5-BENZOTHIAZEPINE DERIVATIVES AND PREPARATION THEREOF

[75] Inventors: Akiyoshi Kawai, Aichi; Hirozumi Inoue, Tokyo; Hiroshi Narita, Urawa; Taku Nagao, Tokyo, all of Japan

[73] Assignee: Tanabe Seiyaku Co., Ltd., Osaka, Japan

[21] Appl. No.: 570,625

[22] Filed: Aug. 21, 1990

[30] Foreign Application Priority Data

Aug. 31, 1989 [JP] Japan .................................. 1-226506

[51] Int. Cl.$^5$ ................... C07D 281/10; A61K 31/55
[52] U.S. Cl. ..................................... 514/211; 540/491
[58] Field of Search .......................... 540/491; 514/211

[56] References Cited

U.S. PATENT DOCUMENTS

| | | | |
|---|---|---|---|
| 3,562,257 | 2/1971 | Kugita et al. | 540/491 |
| 4,729,994 | 3/1988 | Carson | 540/491 |

FOREIGN PATENT DOCUMENTS

| | | |
|---|---|---|
| 0256888 | 8/1987 | European Pat. Off. |
| 0320361 | 12/1987 | European Pat. Off. |
| 63-275572 | 11/1988 | Japan .................... 540/491 |

OTHER PUBLICATIONS

Inoue, Chem. Abs., 110, 231671 (1988).
Inoue, Chemical Abstracts, 110:231671a, p. 653, vol. 110, No. 25 (Jun. 1989).

*Primary Examiner*—Mark L. Berch
*Attorney, Agent, or Firm*—Birch, Stewart, Kolasch & Birch

[57] ABSTRACT

Novel 1,5-benzothiazepine derivatives of the formula:

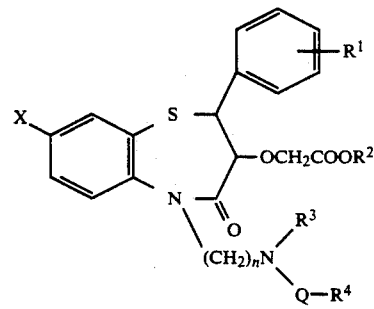

wherein X is hydrogen atom, a halogen atom or a lower alkyl group; $R^1$ is a lower alkyl group or a lower alkoxy group; $R^2$ is hydrogen atom, a lower alkyl group, a substituted or unsubstituted phenyl group, a substituted or unsubstituted phenyl-lower alkyl grup or a diphenyl-lower alkyl group; $R^3$ is a lower alkyl group or a substituted or unsubstituted phenyl-lower alkyl group, Q is single bond, or an alkylene or lower alkenylene group which may optionally be substituted by a lower alkoxy group or oxo group; $R^4$ is (i) hydrogen atom, (ii) a lower alkyl group, (iii) an N-phenyl-N-lower alkylamino group, (iv) a phenyl, phenyloxy, phenylthio, benzenesulfonylamino, 1,4-benzoquinonyl or benzylthio group which may optionally have substituent, or (v) a heterocyclic group which may optionally have substituent; and n is 2 or 3, or a pharmaceutically acceptable salt thereof, which are useful as a calcium antagonist, and the process for preparing thereof.

11 Claims, No Drawings

1,5-BENZOTHIAZEPINE DERIVATIVES AND PREPARATION THEREOF

This invention relates to novel 1,5-benzothiazepine derivatives which are useful as a calcium antagonist.

PRIOR ART

Hitherto, calcium antagonists having coronary vasodilating effect, improving effect on myocardial ischemia and hypotensive effect have widely been used for prophylaxis and treatment of various cardiovascular diseases (cf. U.S. Pat. No. 3,562,257), and in this field, most attention has been given to developing a drug with strong effects and a long duration of action. However, for treating patients with critical cardiovascular diseases, occasionally, a drug with an ultrashort duration of action is rather more preferable than ones with a long duration of action. Thus, it has also been required to develop a calcium antagonist which can exhibit calcium antagonistic effect immediately after the administration thereof and thereafter lose the said effect rapidly.

BRIEF DESCRIPTION OF THE INVENTION

The present invention relates to novel 1,5-benzothiazepine derivatives which can exhibit excellent calcium antagonistic effect with short duration of action. The invention provides also a pharmaceutical preparation for the prophylaxis and treatment of various cardiovascular diseases containing said novel compound as an active ingredient. The invention provides further procedures for preparing the novel 1,5-benzothiazepine derivatives and also provides novel intermediate compounds thereof.

DETAILED DESCRIPTION OF THE INVENTION

The present invention relates to novel 1,5-benzothiazepine derivatives of the formula:

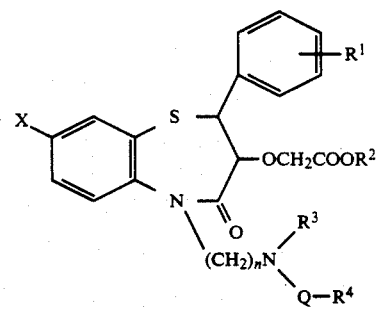

(I)

wherein X is hydrogen atom, a halogen atom or a lower alkyl group; $R^1$ is a lower alkyl group or a lower alkoxy group; $R^2$ is hydrogen atom, a lower alkyl group, a substituted or unsubstituted phenyl group, a substituted or unsubstituted phenyl-lower alkyl group or a diphenyl-lower alkyl group; $R^3$ is a lower alkyl group or a substituted or unsubstituted phenyl-lower alkyl group; Q is a single bond, or an alkylene or lower alkenylene group which may optionally be substituted by a lower alkoxy group or oxo group; $R^4$ is (i) hydrogen atom, (ii) a lower alkyl group, (iii) an N-phenyl-N-lower alkylamino group, (iv) a phenyl, phenyloxy, phenylthio, benzenesulfonylamino, 1,4-benzoquinonyl or benzylthio group which may optionally have one or more substituents, or (v) a heterocyclic group which may optionally have one or more substituents; and n is 2 or 3, or a pharmaceutically acceptable salt thereof.

The desired compounds (I) of the present invention are useful as a calcium antagonist. As compared with the known compound, for example, one disclosed in U.S. Pat. No. 3,562,257, the compounds (I) of the present invention are characterized in that the duration time of action is extremely shorter, and that they show a strong calcium antagonistic effect immediately after the administration thereof, and lose rapidly said effect thereafter.

The desired compounds of the present invention include the compounds of the formula (I), wherein $R^2$ is hydrogen atom, a lower alkyl group, a halogenophenyl group, a diphenyl-lower alkyl group, or a phenyl-lower alkyl group which may optionally be substituted by 1-2 groups selected from a lower alkyl group, a lower alkoxy group, a halogen atom and nitro group; $R^3$ is a lower alkyl group or a phenyl-lower alkyl group which may optionally be substituted by a lower alkyl group; $R^4$ is (i) hydrogen atom, (ii) a lower alkyl group, (iii) an N-phenyl-N-lower alkylamino group, (iv) a phenyl, phenyloxy, phenylthio, benzenesulfonylamino, 1,4-benzoquinonyl or benzylthio group which may optionally be substituted by 1-3 groups selected from a lower alkyl group, a lower alkoxy group, hydroxyl group, a trihalogenomethyl group, a halogen atom, a lower alkoxycarbonyl group, cyano group, a di-lower alkylamino group, a lower alkylsulfonylamino group and a lower alkanoylamino group, or by methylenedioxy group, (v) thienyl group, furyl group, pyridyl group, pyrrolidinyl group, a piperidinyl group having optionally a lower alkanoyl substituent, morpholinyl group, or a homopiperazinyl group having optionally a diphenyl-lower alkyl substituent, (vi) a benzothiophenyl group having optionally a halogen substituent, (vii) an indolyl group having optionally a lower alkyl substituent, or (viii) dihydrobenzofuranyl group.

In the above-mentioned compound of the present invention, the lower alkoxy group, the lower alkyl group, the alkylene group, the lower alkenylene group and the lower alkanoyl group include an alkoxy group of one to six carbon atoms, an alkyl group of one to six carbon atoms, an alkylene group of one to ten carbon atoms, an alkenylene group of two to six carbon atoms and an alkanoyl group of two to six carbon atoms, respectively. Preferred examples of these groups are the groups of less than four carbon atoms. The desired compounds (I) of the present invention also include two stereoisomers, four optical isomers or a mixture thereof owing to an asymmetric carbon atom thereof. Among said isomers, however, the cis isomer, especially the (+)-cis isomer of the compound (I) is preferred for medical use.

The desired compounds (I) of the present invention can be prepared by condensing a compound of the formula:

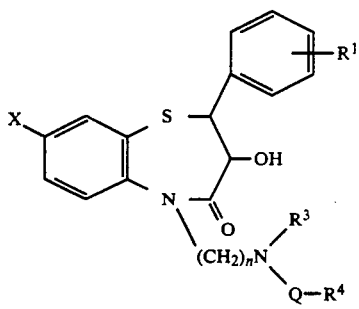

wherein X, $R^1$, $R^3$, Q, $R^4$ and n are the same as defined above, with an acetic acid derivative of the formula:

$$Y^1-CH_2COOR^2 \qquad (III)$$

wherein $Y^1$ is a reactive residue and $R^2$ is the same as defined above.

The desired compounds (I) wherein $R^2$ is hydrogen atom can be prepared by hydrolysis or reduction of a compound of the formula:

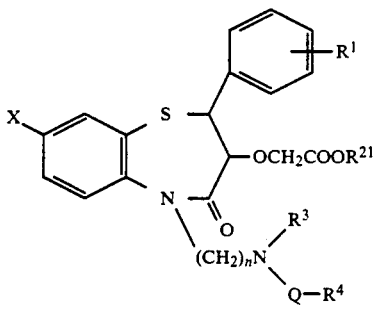

wherein $R^{21}$ is a lower alkyl group, a substituted or unsubstituted phenyl group, a substituted or unsubstituted phenyl-lower alkyl group or a diphenyl-lower alkyl group, and X, $R^1$, $R^3$, Q, $R^4$ and n are the same as defined above.

Further, the desired compounds (I) of the present invention wherein $R^2$ is a lower alkyl group, a substituted or unsubstituted phenyl group, a substituted or unsubstituted phenyl-lower alkyl group or a diphenyl-lower alkyl group can be prepared by condensing a carboxylic acid compound of the formula:

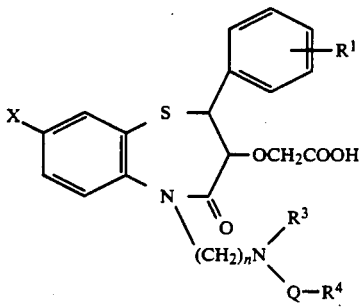

wherein X, $R^1$, $R^3$, Q, $R^4$ and n are the same as defined above, or a reactive derivative at the carboxyl moiety thereof with an alcohol compound of the formula:

$$HO-R^{21} \qquad (IV)$$

wherein $R^{21}$ is the same as defined above.

Moreover, the desired compounds (I) of the present invention wherein Q is a single bond and $R^4$ is hydrogen atom can be prepared by reacting a compound of the formula:

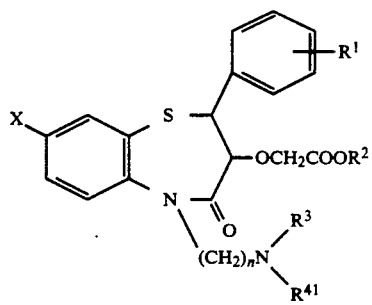

wherein $R^{41}$ is a lower alkyl group, X, $R^1$, $R^2$, $R^3$ and n are the same as defined above, with an acid halide or ester of a halogenoformic acid, to give a compound of the formula:

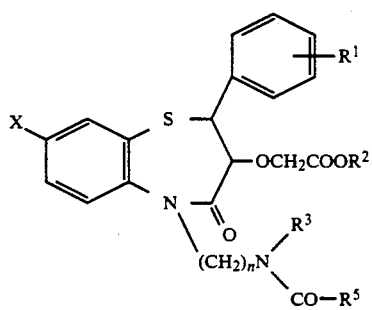

wherein $R^5$ is a halogen atom or an ester residue, and X, $R^1$, $R^2$, $R^3$ and n are the same as defined above, followed by removing the N-substituted acyl group: $-CO-R^5$ from the above compound (V).

Alternatively, the desired compounds (I) of the present invention can also be prepared by reacting a compound of the formula:

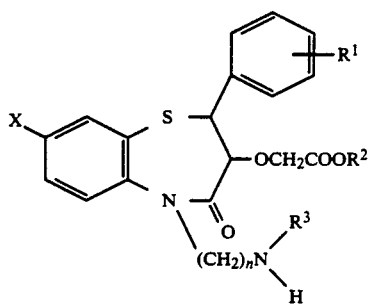

wherein X, $R^1$, $R^2$, $R^3$ and n are the same as defined above, with a compound of the formula:

$$Y^2-Q^2-R^4 \qquad (VI)$$

wherein $Y^2$ is a reactive residue; $Q^2$ is a single bond, or an alkylene or lower alkenylene group which may optionally be substituted by a lower alkoxy group or oxo group; and $R^4$ is the same as defined above, and when $Q^2$ is an alkylene or lower alkenylene group which is substituted by oxo group, by further optionally reducing the reaction product.

The condensation reaction between the starting compounds (II) and (III) may be carried out in the presence of an acid scavenger. The acid scavenger includes alkali metal hydrides, alkali metal hydroxides, alkali metal amides, organic amines (e.g. triethylamine, etc.), and the like. Examples of reactive residue for $Y^1$ are halogen atoms (e.g. chlorine, bromine, etc.). This reaction is preferably carried out in the presence of a solvent such as benzene, toluene, tetrahydrofuran, dioxane, dimethylformamide, dimethylsulfoxide, hexamethylphosphoric triamide, and the like. This reaction may preferably be carried out under cooling or heating, more preferably at a temperature of 20° C. to 60° C.

The hydrolysis or reduction reaction of the compound (I-a) may be carried out by a conventional method. For example, the hydrolysis is preferably carried out in the presence of a base (e.g. alkali metal hydroxides, alkali metal carbonates, alkali metal hydrogen carbonates, etc.) or an acid (e.g. inorganic acids, etc.). The reduction reaction may be carried out by subjecting the compound (I-a) to catalytic reduction in the presence of a suitable catalyst (e.g. palladium-carbon, etc.). When the hydrolysis is employed, it is desirable to carry out in water or a mixed solvent of water and a lower alkanol, and when the reduction reaction is employed, it is desirable to carry out in a lower alkanol, diethyl ether, tetrahydrofuran, dioxane, and the like. These reactions may be carried out under cooling or heating, preferably at room temperature or with warming.

The condensation reaction between the carboxylic acid compound (I-b) and the alcohol compound (IV) may be carried out in the presence of a dehydrating agent. The dehydrating agent includes conventional dehydrating agents such as dicyclohexylcarbodiimide, and the like. The condensation reaction is preferably carried out in the presence of a catalyst such as 4-dimethylaminopyridine, 1-hydroxybenzotriazole, and the like. On the other hand, the condensation reaction between a reactive derivative at the carboxyl moiety of the carboxylic acid compound (I-b) and the alcohol compound (IV) may be carried out in the presence or absence of an acid scavenger. The acid scavenger includes any conventional ones such as pyridine, triethylamine, and the like. The reactive derivative at carboxyl moiety of the carboxylic acid compound (I-b) are, for example, acid halides. These condensation reactions are preferably carried out in the presence or absence of a suitable solvent (e.g. methylene chloride, chloroform, benzene, toluene, tetrahydrofuran, dioxane, diethyl ether, pyridine, dimethylformamide, etc.) under cooling or warming, more preferably under cooling or at room temperature.

The reaction between the compound (I-c) and an acid halide or ester of a halogenoformic acid may be carried out in the presence or absence of a base. Examples of the base are triethylamine, pyridine, tetramethylurea, hexamethylphospholic triamide, quinoline, and the like. Examples of the solvent are toluene, n-hexane, diethyl ether, tetrahydrofuran, dioxane, acetone, methylene chloride, and the like. This reaction is preferably carried out under cooling or heating, more preferably at room temperature. The subsequent removal of N-substituted acyl group from the compound (V) is preferably carried out by warming or heating the compound (V) in water or a mixed solvent of water and a suitable organic solvent (e.g. a lower alkanol, acetonitrile, acetic acid, tetrahydrofuran, dioxane, acetone, etc.).

The reaction between the compound (I-d) and the starting compound (VI) may be carried out in the presence or absence of an acid scavenger. The acid scavenger includes the same agents as used in the condensation reaction between the starting compounds (II) and (III). Examples of the reactive residue for $Y^2$ are halogen atom, methanesulfonyloxy group, toluenesufonyloxy group, trifluoromethanesulfonyloxy group, and the like. This reaction is preferably carried out under cooling or heating in the presence of a suitable solvent (e.g. methylene chloride, chloroform, water, etc., or a mixture thereof). The subsequent optional reduction reaction is preferably carried out at room temperature or with heating in the presence of a reducing agent (e.g. diborane, borane dimethylsulfide, etc.) in a suitable solvent (e.g. tetrahydrofuran, diethyl ether, etc.).

Besides, in the above reactions of the present invention, the starting compounds (I-a), (I-b), (I-c), (I-d), (II) and (V) may be used either in the free form or in the form of a salt thereof such as organic acid addition salts, inorganic acid addition salts, and the like, if required.

Thus-obtained desired compounds (I) of the present invention and a salt thereof show an excellent calcium antagonistic effect, and exhibit various excellent properties as an ultrashort-acting calcium antagonist, that is, exhibit rapidly the strong calcium antagonistic effect immediately after the administration thereof and lose rapidly the said effect thereafter. The desired compounds (I) of the present invention can be used as a coronary vasodilator, a cerebral vasodilator, a hypotensive agent, a tissue protecting agent, an antiarrhythmic agent. For example, when a compound (I) of the present invention; (+)-cis-2-(4-methoxyphenyl)-3-(ethoxycarbonylmethyl)oxy-5-{2-[N-methyl-N-(3-methoxyphenethyl)amino]ethyl}-2,3-dihydro-1,5-benzothiazepin-4(5H)-one fumarate (20 μg/kg) was administered intravenously to a mature dog under pentobarbital anesthesia over a period of 60 minutes, and the increasing effect thereof on the vertebral artery blood stream was examined, it increased the vertebral artery blood stream by about 180% during the medication, and the increase in the blood stream was reduced by half at nine minutes after the end of the administration. According to the above-mentioned properties, the desired compounds (I) of the present invention offer the advantages that when the compounds are administered to aged patients, patients with serious cardiovascular diseases or patients with angina pectoris who require the emergency care, the myocardial ischemia is rapidly improved, and the burden on the heart is moderated, and further that the physicians can modify the dose thereof according to the patient's response level thereto, so that they can control the function of the patient's heart as they wish. Moreover, when undesirable effects, such as the dangerously low level of the heart rate, and the like are observed, the effects of the compounds (I) of the present invention can rapidly be dissipated by stopping the administration thereof, so that the compounds (I) of the present invention can be used safely even for patients with a critical symptom.

Moreover, the operations for the aged patients or patients with an ischemic heart disease or hypertension, and the open heart surgery or the organ transplantation occasionally cause abnormal hypertension in the patients, which may further cause the increase in the burden onto the myocardium, the increase in the oxygen consumption of the myocardium, arrhythmia (irregular pulse), the breakdown of the blood vessel, the bleeding in the operated part, or subsequent cardiac insufficiency after the operation especially in the aged patients. And sometimes the brain injury due to the microemboli-induced cerebral ischemia is experienced during the operation. However, when the desired compounds (I) of the present invention are used, the physicians can control the blood pressure of patients rapidly and precisely as they wish and they can protect the brain from ischemic injury even during the operation, and after the operation, the drug effect thereof can be easily and rapidly dissipated. Therefore, the desired compounds (I) of the present invention or a pharmaceutically acceptable salt thereof can effectively be used for the emergency treatment of the abnormal hypertension and the control of the blood pressure during the operation, the protection of injury caused by the re-perfusion during the reproduction of the coronary blood vessel, the protection of the heart during the open heart surgery and the protection of the organ (e.g. heart, liver, kidney, etc.) during the transplantation, and the like.

In addition, the desired compounds (I) of the present invention or a pharmaceutically acceptable salt thereof can effectively be used for the treatment of cerebrovascular vasospasm such as that encountered after neurosurgery or subarachnoid hemorrhage.

In the treatment of thrombosis, the desired compounds (I) of the present invention or a pharmaceutically acceptable salt thereof can effectively be used in the form of an injection preparation which is incorporated with a thrombolytic agent.

Furthermore, the desired compounds (I) of the present invention show advantageously low toxicity, and almost no atrioventricular conduction disturbance effect.

In particular, the desired compounds (I) of the present invention are quite advantageous in that, as compared with the known compounds, they have higher safety margin between the therapeutic effect (a coronary vasodilating effect and a hypotensive effect) and the side effect (atrioventricular conduction disturbance effect) and can be used as a ultra-short calcium antagonist without substantial undesirable side effect.

The desired compounds (I) of the present invention can be used for medical use either in the free form or in the form of a pharmaceutically acceptable salt thereof. Suitable examples of pharmaceutically acceptable salts of the compounds (I) are salts with inorganic acids such as hydrochloric acid, hydrobromic acid, hydriodic acid, perchloric acid, sulfuric acid, phosphoric acid, and the like, and salts with organic acids such as oxalic acid, maleic acid, fumaric acid, tartaric acid, methanesulfonic acid, and the like.

The desired compounds (I) of the present invention and a pharmaceutically acceptable salt thereof can be administered orally in the form of a pharmaceutical preparation such as tablets, granules, capsules or powder, but more preferably parenterally in the form of an injection preparation.

The dose of the desired compounds (I) of the present invention or a pharmaceutically acceptable salt thereof may vary depending on the administration route employed, the age, weight or the conditions of patients and the kind of diseases to be treated. In general, the preferred dose of the desired compounds (I) of the present invention or a pharmaceutically acceptable salt thereof may be about 0.01–10 mg/kg, especially about 0.01–2 mg/kg by parenteral route (e.g. intravenous injection).

The starting compounds (II) of the present invention can be prepared by condensing a compound of the formula:

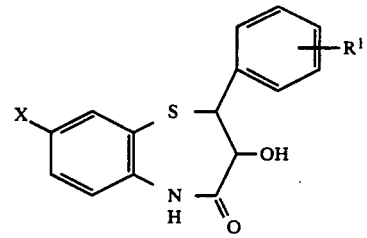

wherein X and $R^1$ are the same defined above, with a compound of the formula:

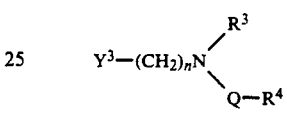

wherein $Y^3$ is a reactive residue, and $R^3$, Q, $R^4$ and n are the same as defined above, in the presence of an acid scavenger under cooling or heating, or by condensing a compound of the formula:

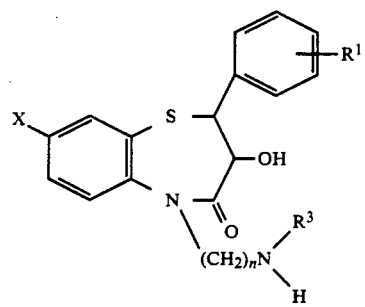

wherein X, $R^1$, $R^3$ and n are the same as defined above, or a salt thereof with a compound of the formula:

(IX)

wherein $Y^4$ is a reactive residue, and Q and $R^4$ are the same as defined above, in the presence or absence of an acid scavenger under cooling or heating.

The present invention is illustrated in detail by the following Examples but should not be construed to be limited thereto.

EXAMPLE 1

(1) A mixture of (+)-cis-2-(4-methoxyphenyl)-3-hydroxy-8-chloro-2,3-dihydro-1,5-benzothiazepin-4(5H)-one (6.8 g), 2-(dimethylamino)ethyl chloride hydrochloride (3.02 g), potassium carbonate (6.1 g) and acetone (150 ml) is stirred under refluxing for 20 hours. After the completion of the reaction, the insoluble materials are removed by filtration and the filtrate is concentrated under reduced pressure. The resulting residue is dissolved in ethyl acetate, washed with water, dried and the ethyl acetate is distilled off. The resulting residue is recrystallized from a mixture of ethyl acetate and n-hexane to give (+)-cis-2-(4-methoxyphenyl)-3-hydroxy-5-[2-(dimethylamino)ethyl]-8-chloro-2,3-dihydro-1,5-benzothiazepin-4(5H)-one (7.13 g) as colorless needles, m.p. 122°-124° C. (decomposed).

(2) To a solution of this product (3.26 g) in dioxane (40 ml) is added 60% sodium hydride (dispersed in oil) (0.40 g). This mixture is stirred at 50° C. for 40 minutes, and then, thereto is added dropwise a solution of t-butyl bromoacetate (1.72 g) in dioxane (20 ml) at the same temperature over a period of ten minutes, and the mixture is stirred for two more hours. After the completion of the reaction, water is added to the reaction mixture and the mixture is extracted with ethyl acetate. The extract is washed and dried, and the solvent is distilled off. The resulting residue is purified by silica gel column chromatography (eluent; chloroform: isopropyl alcohol=100:6) to give (+)-cis-2-(4-methoxyphenyl)-3-(t-butoxycarbonylmethyl)oxy-5-[2-(dimethylamino)ethyl]-8-chloro-2,3-dihydro-1,5-benzothiazepin-4(5H)-one (3.48 g), m.p. 83°-84° C.

IR$\nu$ (nujol): 1740, 1670 cm$^{-1}$.
[$\alpha$]$_D^{20}$+69.7° (c=0.515, methanol).
Fumarate: White powder.
Mass (m/z): 523, 521 (M$^+$).
IR$\nu$ (nujol): 3400, 2800—2400, 1740, 1680 cm$^{-1}$.
[$\alpha$]$_D^{20}$+29.4° (c=0.5, methanol).

EXAMPLES 2-26

(1) The compounds of the following Tables 1 and 2 are obtained by treating the corresponding starting compounds in the same manner as in Example 1-(1).

TABLE 1

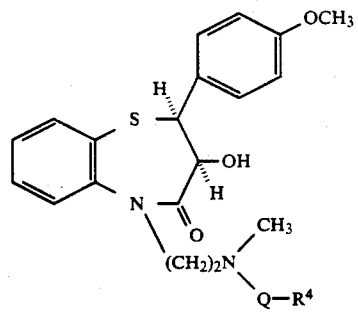

| Ex. No. | —Q—R$^4$ | Physicochemical Properties |
|---|---|---|
| 2-(1) | —(CH$_2$)$_2$—C$_6$H$_4$—OCH$_3$ (para) | Oil<br>IR*$^1$: 1670, 1510, 1250 cm$^{-1}$<br>Mass: 493 (MH$^+$) |
| 3-(1) | —(CH$_2$)$_2$—C$_6$H$_4$—OCH$_3$ (meta) | Oil<br>IR*$^1$: 1680, 1510, 1250 cm$^{-1}$<br>Mass: 493 (MH$^+$) |
| 4-(1) | —(CH$_2$)$_3$—C$_6$H$_5$ | Oil<br>IR*$^1$: 1680, 1510, 1250 cm$^{-1}$<br>Mass: 477 (MH$^+$) |

TABLE 1-continued

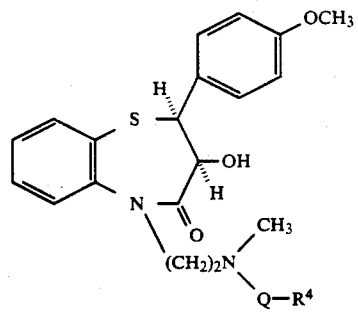

| Ex. No. | —Q—R$^4$ | Physicochemical Properties |
|---|---|---|
| 5-(1) | —(CH$_2$)$_2$—C$_6$H$_4$—CH$_3$ (para) | Oil<br>IR*$^1$: 3500, 2950, 1670, 1510, 1250 cm$^{-1}$<br>Mass: 477 (MH$^+$) |
| 6-(1) | —(CH$_2$)$_2$—C$_6$H$_2$(OCH$_3$)$_3$ (2,3,4-tri) | Oil<br>IR*$^1$: 3490, 2950, 1660, 1510, 1250 cm$^{-1}$<br>Mass: 553 (MH$^+$) |
| 7-(1) | —(CH$_2$)$_3$—C$_6$H$_3$(OCH$_3$)$_2$ (2,3-di) | Oil<br>IR*$^1$: 3490, 2950, 1660, 1510, 1250, 1030 cm$^{-1}$<br>Mass: 537 (MH$^+$) |
| 8-(1) | —(CH$_2$)$_2$—C$_6$H$_3$(OCH$_3$)$_2$ (3,4-di) | Hydrochloride:<br>Powder<br>IR*$^2$: 3300, 2800-2200, 1680, 1580 cm$^{-1}$<br>Mass: 523 (MH$^+$) |
| 9-(1) | —CH$_2$-(2-thienyl) | Oil<br>IR*$^1$: 1660, 1510, 1250 cm$^{-1}$<br>Mass: 455 (MH$^+$) |
| 10-(1) | —(CH$_2$)$_2$-(2-thienyl) | Oil<br>IR*$^1$: 1660, 1510, 1250 cm$^{-1}$<br>Mass: 469 (MH$^+$) |
| 11-(1) | —(CH$_2$)$_2$-(3-thienyl) | Oil<br>IR*$^1$: 2950, 1660, 1510, 1250, 1180, 760 cm$^{-1}$<br>Mass: 469 (MH$^+$) |
| 12-(1) | —(CH$_2$)$_2$-(3-pyridyl) | Oil<br>IR*$^1$: 2950, 1665, 1610, 1510, 1250, 1180, 790 cm$^{-1}$<br>Mass: 464 (MH$^+$) |
| 13-(1) | —(CH$_2$)$_2$-(2-pyridyl) | Oil<br>IR*$^1$: 2950, 1665, 1510, 1250, 760 cm$^{-1}$<br>Mass: 463 (M$^+$), 462 (M$^+$ − 1) |
| 14-(1) | —(CH$_2$)$_2$-(4-pyridyl) | Oil<br>IR*$^1$: 2950, 1665, 1605, 1510, 1250 cm$^{-1}$<br>Mass: 464 (MH$^+$) |

TABLE 1-continued

[Structure: benzothiazepine core with 4-methoxyphenyl substituent, OH, and N-CH3-(CH2)2-N-Q-R4 side chain]

| Ex. No. | —Q—R⁴ | Physicochemical Properties |
|---|---|---|
| 15-(1) | —(CH₂)₃—[3-OCH₃-phenyl] | Oil<br>IR*¹: 2950, 1660, 1510, 1250, 1180, 1040 cm⁻¹<br>Mass: 506 (M⁺) |
| 16-(1) | —(CH₂)₂—[1-methylindol-3-yl] | Oil<br>Mass: 516 (MH⁺) |
| 17-(1) | —(CH₂)₄—[4-OCH₃-phenyl] | Oil<br>IR*¹: 3480, 1660, 1510, 1250 cm⁻¹<br>Mass: 520 (M⁺) |
| 18-(1) | —(CH₂)₃—[4-OCH₃-phenyl] | Oil<br>IR*¹: 3470, 1660, 1510, 1250 cm⁻¹<br>Mass: 506 (M⁺) |
| 19-(1) | —(CH₂)₂—[2-OCH₃-phenyl] | Oil<br>IR*¹: 3470, 1660, 1250 cm⁻¹<br>Mass: 493 (MH⁺) |
| 20-(1) | —(CH₂)₂—O—[phenyl] | Oil<br>IR*¹: 3470, 1660, 1250 cm⁻¹<br>Mass: 479 (MH⁺) |
| 21-(1) | —(CH₂)₂—S—[phenyl] | Oil<br>IR*¹: 3460, 1600 cm⁻¹<br>Mass: 494 (M⁺) |
| 22-(1) | —(CH₂)₃—[4-CH₃-phenyl] | IR*¹: 3460, 1660, 1610, 1510 cm⁻¹<br>Mass: 490 (M⁺) |
| 23-(1) | —(CH₂)₃—[3-CH₃-phenyl] | IR*¹: 3480, 1660, 1610, 1515 cm⁻¹<br>Mass: 490 (M⁺) |
| 24-(1) | —(CH₂)₄—[4-CH₃-phenyl] | IR*¹: 3480, 1660, 1610, 1510, 1470 cm⁻¹<br>Mass: 504 (M⁺) |

IR*¹: IRν (liquid) (hereinafter, the same)
IR*²: IRν (nujol) (hereinafter, the same)

TABLE 2

[Structure: benzothiazepine core with X substituent on benzo ring, R¹ substituent on phenyl, OH, and N-CH3-(CH2)2-N-(CH2)2-[3,4-dimethoxyphenyl] side chain]

| Ex. No. | X | R¹ | Physicochemical Properties |
|---|---|---|---|
| 25-(1) | Cl | OCH₃ | Hydrochloride:<br>M.p. 205–207° C.<br>IR*²: 3470, 1660, 1605, 1590, 1580 cm⁻¹<br>Mass: 557 (MH⁺) |
| 26-(1) | CH₃ | CH₃ | Hydrochloride:<br>M.p. 223–225° C.<br>Mass: 521 (MH⁺) |

(2) The compounds of the following Tables 3–5 are obtained by treating the above products (1) in the same manner as in Example 1-(2).

TABLE 3

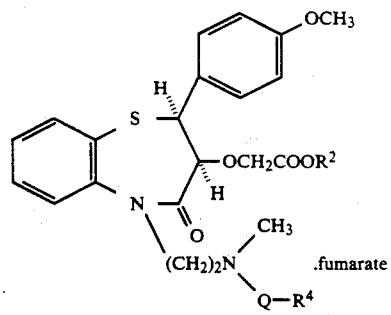

.fumarate

| Ex. No. | R² | —Q—R⁴ | Physicochemical Properties |
|---|---|---|---|
| 2-(2) | —CH₂CH₃ | —(CH₂)₂—C₆H₄—OCH₃ (para) | IR*²: 1700, 1670, 1511, 1250 cm⁻¹<br>Mass: 579 (MH⁺)<br>$[\alpha]_D^{20}$ +66.7° (c = 0.3, methanol) |
| 3-(2) | —CH₂CH₃ | —(CH₂)₂—C₆H₄—OCH₃ (meta) | IR*²: 1670, 1510, 1250 cm⁻¹<br>Mass: 576 (M⁺ − 2)<br>$[\alpha]_D^{20}$ +71.7° (c = 0.3, methanol) |
| 4-(2) | —CH₂CH₃ | —(CH₂)₃—C₆H₅ | IR*²: 1670, 1510, 1250, 1030, 980 cm⁻¹<br>Mass: 562 (M⁺)<br>$[\alpha]_D^{20}$ +68.0° (c = 0.3, methanol) |
| 5-(2) | —CH₂CH₃ | —(CH₂)₂—C₆H₄—CH₃ | IR*²: 1705, 1670, 1510 cm⁻¹<br>Mass: 563 (MH⁺)<br>$[\alpha]_D^{20}$ +82.3° (c = 0.3, methanol) |
| 6-(2) | —CH₂CH₃ | —(CH₂)₂—C₆H₂(OCH₃)₃ | IR*²: 1710, 1665, 1560, 1510 cm⁻¹<br>Mass: 639 (MH⁺)<br>$[\alpha]_D^{20}$ +71.0° (c = 0.3, methanol) |
| 7-(2) | —CH₂CH₃ | —(CH₂)₃—C₆H₃(OCH₃)₂ | IR*²: 1710, 1670, 1515, 1260 cm⁻¹<br>Mass: 623 (MH⁺)<br>$[\alpha]_D^{20}$ +58.0° (c = 0.3, methanol) |
| 8-(2) | —CH₂—C₆H₅ | —(CH₂)₂—C₆H₃(OCH₃)₂ | IR*²: 1670, 1510, 1250, 1130 cm⁻¹<br>Mass: 671 (MH⁺)<br>$[\alpha]_D^{20}$ +49.00° (c = 0.3, methanol) |
| 9-(2) | —CH₂CH₃ | —CH₂—(2-thienyl) | IR*²: 1710, 1670, 1510, 1250, 1180 cm⁻¹<br>Mass: 541 (MH⁺)<br>$[\alpha]_D^{20}$ +73.3° (c = 0.3, methanol) |
| 10-(2) | —CH₂CH₃ | —(CH₂)₂—(2-thienyl) | IR*²: 1705, 1675, 1380, 1250, 1030 cm⁻¹<br>Mass: 555 (MH⁺)<br>$[\alpha]_D^{20}$ +72.7° (c = 0.3, methanol) |
| 11-(2) | —CH₂CH₃ | —(CH₂)₂—(3-thienyl) | IR*²: 1745, 1705, 1670, 1510, 1250, 1180 cm⁻¹<br>Mass: 555 (MH⁺)<br>$[\alpha]_D^{20}$ +69.0° (c = 0.3, methanol) |

TABLE 3-continued

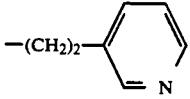
.fumarate

| Ex. No. | R² | —Q—R⁴ | Physicochemical Properties |
|---|---|---|---|
| 12-(2) | —CH₂CH₃ | —(CH₂)₂-(3-pyridyl) | IR*²: 2950, 1740, 1670, 1460, 1250 cm⁻¹<br>Mass: 550 (MH⁺)<br>$[\alpha]_D^{20}$ +64.3° (c = 0.3, methanol) |
| 13-(2) | —CH₂CH₃ | —(CH₂)₂-(2-pyridyl) | Difumarate:<br>IR*²: 1745, 1700, 1670 cm⁻¹<br>Mass: 550 (MH⁺)<br>$[\alpha]_D^{20}$ +46.0° (c = 0.3, methanol) |
| 14-(2) | —CH₂CH₃ | —(CH₂)₂-(4-pyridyl) | Difumarate:<br>IR*²: 1745, 1670, 1510, 1255, 1140 cm⁻¹<br>Mass: 550 (MH⁺)<br>$[\alpha]_D^{20}$ +49.0° (c =0.3, methanol) |
| 15-(2) | —CH₂CH₃ | —(CH₂)₃-(3-OCH₃-phenyl) | IR*²: 1750, 1670, 1260, 1140, 1035 cm⁻¹<br>Mass: 593 (MH⁺)<br>$[\alpha]_D^{20}$ +54.3° (c = 0.3, methanol) |
| 16-(2) | —CH₂CH₃ | —(CH₂)₂-(1-methylindol-3-yl) | IR*²: 2900, 1740, 1710, 1670, 1250 cm⁻¹<br>Mass: 602 (MH⁺)<br>$[\alpha]_D^{20}$ +55.0° (c = 0.2, methanol) |
| 17-(2) | —CH₂CH₃ | —(CH₂)₄-(4-OCH₃-phenyl) | IR*²: 1740, 1670, 1510, 1250 cm⁻¹<br>Mass: 607 (MH⁺)<br>$[\alpha]_D^{20}$ +57.1° (c = 0.247, methanol) |
| 18-(2) | —CH₂CH₃ | —(CH₂)₃-(4-OCH₃-phenyl) | IR*²: 1740, 1710, 1670, 1510, 1250 cm⁻¹<br>Mass: 593 (MH⁺)<br>$[\alpha]_D^{20}$ +53.9° (c = 0.218, methanol) |
| 19-(2) | —CH₂CH₃ | —(CH₂)₂-(2-OCH₃-phenyl) | IR*²: 1740, 1710, 1680, 1510, 1250 cm<¹<br>Mass: 579 (MH⁺)<br>$[\alpha]_D^{20}$ +60.4° (c = 0.275, methanol) |
| 20-(2) | —CH₂CH₃ | —(CH₂)₂—O—phenyl | IR*²: 1740, 1670, 1510, 1250 cm<¹<br>Mass: 565 (MH⁺)<br>$[\alpha]_D^{20}$ +63.1° (c = 0.241, methanol) |
| 21-(2) | —CH₂CH₃ | —(CH₂)₂—S—phenyl | IR*²: 1740, 1700, 1670, cm⁻¹<br>Mass: 581 (MH⁺)<br>$[\alpha]_D^{20}$ +72.9° (c = 0.328, methanol) |

TABLE 3-continued

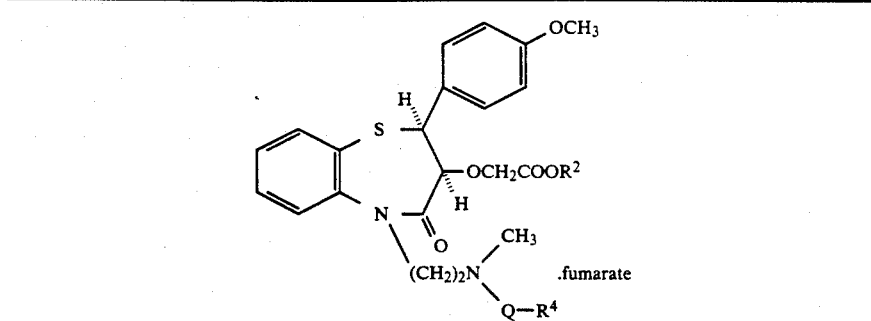

.fumarate

| Ex. No. | R² | —Q—R⁴ | Physicochemical Properties |
|---|---|---|---|
| 22-(2) | —CH₂CH₃ | —(CH₂)₃—⟨C₆H₄⟩—CH₃ (para) | IR*²: 1740, 1700, 1670, 1640, 1510, 1460, 1250 cm⁻¹<br>Mass: 577 (MH⁺)<br>[α]$_D^{20}$ +53.7° (c = 0.205, methanol) |
| 23-(2) | —CH₂CH₃ | —(CH₂)₃—⟨C₆H₄⟩—CH₃ (meta) | IR*²: 1750, 1710, 1670, 1640, 1510, 1460, 1380, 1260 cm⁻¹<br>Mass: 577 (MH⁺)<br>[α]$_D^{20}$ +49.1° (c = 0.432, methanol) |
| 24-(2) | —CH₂CH₃ | —(CH₂)₄—⟨C₆H₄⟩—CH₃ (para) | IR*²: 1740, 1705, 1670, 1640, 1510, 1250 cm⁻¹<br>Mass: 591 (MH⁺), 487<br>[α]$_D^{20}$ +55.8° (c = 0.312, methanol |

TABLE 4

(structure: X-substituted benzothiazepine with R¹ on phenyl, OCH₂CO₂CH₂CH₂ linker to dimethoxyphenyl-propylamine group) .fumarate

| Ex. No. | X | R¹ | Physicochemical Properties |
|---|---|---|---|
| 25-(2) | Cl | OCH₃ | IR*²: 1750, 1700, 1680 cm⁻¹<br>Mass: 644 (MH⁺)<br>[α]$_D^{20}$ +38.1° (c = 0.452, methanol) |
| 26-(2) | CH₃ | CH₃ | IR*²: 1750, 1700, 1670 cm⁻¹<br>Mass: 607 (MH⁺)<br>[α]$_D^{20}$ +60.2° (c = 0.321, methanol) |

EXAMPLES 27-28

The compounds of the following Table 5 are obtained by treating the corresponding starting compounds in the same manner as in Example 1-(2).

TABLE 5

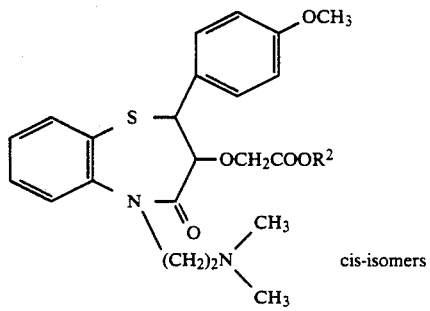

cis-isomers

| Ex. No. | R² | Physicochemical Properties |
|---|---|---|
| 27 | CH₃ | Perchlorate:<br>M.p. 118.5-120° C. (decomposed)<br>IR*²: 2740, 2540, 1750, 1665, 1610 cm⁻¹<br>Mass: 444 (M⁺) |
| 28 | —CH₂—⟨C₆H₅⟩ | M.p. 89.5-91.5° C.<br>Fumarate:<br>M.p.: 114.5-117° C. (decomposed)<br>IR*²: 1750, 1710, 1670, 1605 cm⁻¹<br>Mass: 520 (M⁺) |

EXAMPLES 29-38

The compounds of the following Table 6 are obtained by treating the corresponding starting compounds in the same manner as in Example 1.

TABLE 6

Structure (Ex. 29-37):
- Phenyl-X / S / CH-H / phenyl-R¹ / OCH₂COOR² / N-C(=O) / (CH₂)₂N(CH₃)₂

| Ex. No. | X | R¹ | R² | Physiocochemical Properties |
|---|---|---|---|---|
| 29 | H | OCH₃ | CH₃ | Tartrate:<br>IR*²: 3400, 1745, 1610, 1510, 1250, 1130 cm⁻¹<br>Mass: 444 (M⁺), 413<br>$[\alpha]_D^{20}$ +62.5°<br>(c = 0.4, methanol) |
| 30 | H | OCH₃ | —CH₂—C₆H₅ | M.p. 100–101° C.*³<br>Fumarate:<br>IR*²: 1730, 1680, 1580, 1510, 1250 cm⁻¹<br>Mass: 521 (MH⁺), 450<br>$[\alpha]_D^{20}$ +56.5°<br>(c = 0.4, methanol) |
| 31 | H | OCH₃ | —C(CH₃)₃ | Fumarate:<br>IR*²: 3420, 1720, 1680, 1580, 1510, 1250, 1130 cm⁻¹<br>Mass: 487 (MH⁺)<br>$[\alpha]_D^{20}$ +66.5°<br>(c = 0.4, methanol) |
| 32 | Cl | OCH₃ | —CH₂—C₆H₅ | M.p. 97–98° C.<br>Fumarate:<br>IR*²: 3400, 2700–2400, 1740, 1680 cm⁻¹<br>Mass: 557, 555 (M⁺)<br>$[\alpha]_D^{20}$ +39.1°<br>(c = 0.608, methanol) |
| 33 | CH₃ | CH₃ | —CH₂—C₆H₅ | Fumarate:<br>IR*²: 3400, 2700–2400, 1740, 1700, 1680 cm⁻¹<br>Mass: 519 (MH⁺)<br>$[\alpha]_D^{20}$ +59.3°<br>(c = 0.58, methanol) |
| 34 | CH₃ | CH₃ | —C(CH₃)₃ | Fumarate:<br>IR*²: 3450, 2700–2400, 1740, 1700, 1670 cm⁻¹<br>Mass: 485 (MH⁺)<br>$[\alpha]_D^{20}$ +59.8°<br>(c = 0.58, methanol) |
| 35 | H | OCH₃ | —CH(CH₃)₂ | Fumarate:<br>IR*²: 3440, 2630, 2520, 1730, 1710, 1670, 1605 cm⁻¹<br>Mass: 473 (MH⁺)<br>$[\alpha]_D^{20}$ +58.6°<br>(c = 0.99, methanol) |
| 36 | Cl | OCH₃ | —CH(CH₃)₂ | M.p. 68.5–70° C.*³<br>Mass: 508, 510 (MH⁺)<br>Fumarate:<br>IR*²: 3450, 2630, 2520, 1730, 1675, 1605 cm⁻¹<br>$[\alpha]_D^{20}$ +27.7°<br>(c = 0.62, methanol) |
| 37 | CH₃ | CH₃ | —CH(CH₃)₂ | Fumarate:<br>IR*²: 3430, 2720, 2640, 2520, 1735, 1705, 1670, 1570 cm⁻¹<br>Mass: 471 (MH⁺)<br>$[\alpha]_D^{20}$ +65.8°<br>(c = 0.88, methanol) |
| 38 | H | OCH₃ | —CH₂CH₃ | Fumarate:<br>IR*²: 1743, 1701, 1674, 1512, 1254, 1130 cm⁻¹<br>Mass: 459 (MH⁺)<br>$[\alpha]_D^{20}$ +62.3°<br>(c = 0.3, methanol) |

*³: Recrystallized from isopropyl ether/n-hexane

EXAMPLE 39

(1) A mixture of (+)-cis-2-(4-methoxyphenyl)-3-hydroxy-5-[2-(methylamino)ethyl]-2,3-dihydro-1,5-benzothiazepin-4(5H)-one (1.07 g), methylene chloride (20 ml), 3-methoxyphenethyl chloride (500 mg), triethylamine (313 mg) and sodium iodide (30 mg) is stirred at room temperature for 48 hours. After the completion of the reaction, the solvent is distilled off, and the resulting residue is purified by silica gel column chromatography (eluent; chloroform: ethanol=15:1) to give (+)-cis-2-(4-methoxyphenyl)-3-hydroxy-5-{2-[N-methyl-N-(3-methoxyphenethyl)amino]ethyl}-2,3-dihydro-1,5-benzothiazepin-4(5H)-one (625 mg) as oily product.

The physiocochemical properties of this product are the same as those of the desired compound of Example 3-(1).

(2) By treating this product in the same manner as in Example 1-(2), there is obtained (+)-cis-2-(4-methoxyphenyl)-3-(ethoxycarbonylmethyl)oxy-5-{2-[N-methyl-N-(3-methoxyphenethyl)amino]ethyl}-2,3-dihydro-1,5-benzothiazepin-4(5H)-one.

The physicochemical properties of this product are the same as those of the desired product of Example 3-(2).

EXAMPLE 40

(1) A mixture of (+)-cis-2-(4-methoxyphenyl)-3-(ethoxycarbonylmethyl)oxy-5-{2-[N-methyl-N-(4-methoxyphenethyl)amino]ethyl}-2,3-dihydro-1,5-benzothiazepin-4(5H)-one (5.4 g), sodium hydroxide (423 mg), water (50 ml) and methanol (50 ml) is stirred at room temperature overnight. The reaction mixture is concentrated under reduced pressure, and water is added to the resulting residue. The mixture is washed with ether, and the pH value thereof is adjusted to 4 with 10% hydrochloric acid, and then extracted with a mixture of chloroform and isopropyl alcohol. The extract is washed, dried, and the solvent is distilled off to give (+)-cis- 2-(4-methoxyphenyl)-3-(carboxymethyl)oxy-5-{2-[N-methyl-N-(4-methoxyphenethyl)amino]ethyl}-2,3-dihydro-1,5-benzothiazepin-4-(5H)-one (4.57 g) as oily product.

(2) A mixture of this product (1.16 g), methylene chloride (15 ml), p-nitrobenzyl alcohol (306 mg), dicyclohexylcarbodiimide (413 mg) and 4-dimethylaminopyridine (30 mg) is stirred at room temperature for 1 hour. After the completion of the reaction, the insoluble materials are removed by filtration, and the filtrate is concentrated under reduced pressure. The resulting oils residue is purified by silica gel column chromatography (eluent; chloroform: ethanol: ammonium hydroxide=15:1:0.1) to give (+)-cis-2-(4-methoxyphenyl)-3-[(4-nitrobenzyloxy)carbonylmethyl]oxy-5-{2-methyl-N-(4-methoxyphenethyl)-amino]ethyl}-2,3-dihydro-1,5-benzothiazepin-4(5H)-one (1.24 g) as oily product.

Fumarate:
Mass (m/z): 686 (MH+).
IR$\nu$ (nujol): 3320, 1750, 1670, 1510, 1460, 1260 cm$^{-1}$.
$[\alpha]_D^{20}$ +47.7° (c=0.3, methanol).

EXAMPLE 41

(1) By treating (+)-cis-2-(4-methoxyphenyl)-3-(methoxycarbonylmethyl)oxy-5-[2-(dimethylamino)ethyl]-2,3-dihydro-1,5-benzothiazepin-4(5H)-one in the same manner as in Example 40-(1), there is obtained (+)-cis-2-(4-Methoxyphenyl)-3-(carboxymethyl)oxy-5-[2-(dimethylamino)ethyl]-2,3-dihydro-1,5-benzothiazepin-4(5H)-one, m.p. 72°–75° C.

IR$\nu$ (nujol): 3400, 1725, 1670, 1250, 1115 cm$^{-1}$ (2) This product (1.22 g) is refluxed in thionyl chloride (10 ml) for 2 hours, and concentrated under reduced pressure. The oily residue is dissolved in chloroform (20 ml) and thereto is added benzyl alcohol (460 mg). The mixture is stirred for 3 hours, and concentrated under reduced pressure. The resulting residue is purified by silica gel column chromatography (eluent; chloroform: ethanol: ammonium hydroxide=15:1:0.1) to give (+)-cis-2-(4-methoxyphenyl)-3-(benzyloxycarbonylmethyl)oxy-5-[2-(dimethylamino)ethyl]-2,3-dihydro-1,5-benzothiazepin-4(5H)-one (1.07 g).

The physicochemical properties of this product are the same as those of the desired compound of Example 20.

EXAMPLES 42–64

The compounds of the following Table 7 are obtained by treating the corresponding starting compounds in the same manner as in Examples 40 or 41.

TABLE 7

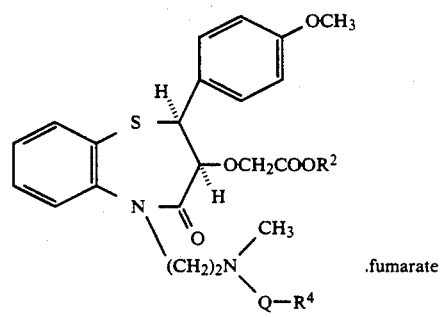

.fumarate

| Ex. No. | R² | —Q—R⁴ | Physicochemical Properties |
|---|---|---|---|
| 42 | —CH₂—⌬—OCH₃ | —CH₃ | IR*²: 1670, 1512, 1250, 1128 cm$^{-1}$<br>Mass: 551 (MH+)<br>$[\alpha]_D^{20}$ +37.0° (c = 0.3, methanol) |
| 43 | —CH₂—⌬—CH₃ | —CH₃ | IR*²: 1705, 1668, 1512, 1252, 1126 cm$^{-1}$<br>Mass: 535 (MH+)<br>$[\alpha]_D^{20}$ +42.3° (c = 0.3, methanol) |
| 44 | —CH₂—⌬—NO₂ | —CH₃ | IR*²: 1751, 1674, 1514, 1377 cm$^{-1}$<br>Mass: 566 (MH+)<br>$[\alpha]_D^{20}$ +53.0° (c = 0.2, methanol) |
| 45 | —CH₂—⌬—Cl | —CH₃ | IR*²: 1733, 1670, 1512, 1254, 1128 cm$^{-1}$<br>Mass: 555 (MH+)<br>$[\alpha]_D^{20}$ +40.66° (c = 0.3, methanol) |
| 46 | —CH₂—⌬(OCH₃)—OCH₃ | —CH₃ | IR*²: 1743, 1733, 1670, 1514, 1255, 1138 cm$^{-1}$<br>Mass: 581 (MH+)<br>$[\alpha]_D^{20}$ +43.3° (c = 0.3, methanol) |

TABLE 7-continued

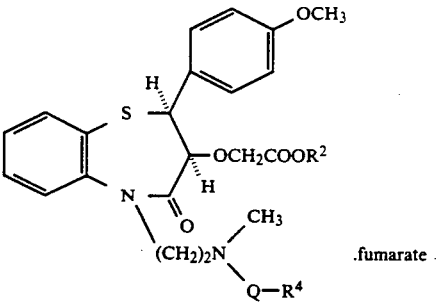

.fumarate

| Ex. No. | R² | —Q—R⁴ | Physicochemical Properties |
|---|---|---|---|
| 47 | —(CH₂)₂—[phenyl] | —CH₃ | IR*²: 1745, 1707, 1668 1511 cm⁻¹<br>Mass: 535 (MH⁺)<br>[α]$_D^{20}$ +46.0° (c = 0.3, methanol) |
| 48 | —(CH₂)₂—[2-nitrophenyl] | —CH₃ | IR*²: 1749, 1707, 1668 cm⁻¹<br>Mass: 580 (MH⁺)<br>[α]$_D^{20}$ +38.0° (c = 0.3, methanol) |
| 49 | [2-chlorophenyl] | —CH₃ | IR*²: 1772, 1670, 1512, 1254, 1119, 762 cm⁻¹<br>Mass: 541 (MH⁺)<br>[α]$_D^{20}$ +54.0° (c = 0.2, methanol) |
| 50 | —(CH₂)₃CH₃ | —CH₃ | IR*²: 1706, 1670, 1512, 1254 cm⁻¹<br>Mass: 487 (MH⁺)<br>[α]$_D^{20}$ +50.0° (c = 0.3, methanol) |
| 51 | —(CH₂)₂CH₃ | —CH₃ | IR*²: 1709, 1668, 1512, 1252 cm⁻¹<br>Mass: 473 (MH⁺)<br>[α]$_D^{20}$ +48.3° (c = 0.3, methanol) |
| 52 | —CH₂—[2,4-dimethylphenyl] | —CH₃ | IR*²: 1734, 1700, 1510, 1252 cm⁻¹<br>Mass: 549 (MH⁺)<br>[α]$_D^{20}$ +40.7° (c = 0.3, methanol) |
| 53 | —CH₂—[4-nitrophenyl] | —(CH₂)₂—[3-methoxyphenyl] | IR*²: 3330, 1750, 1670, 1510, 1250, 1030 cm⁻¹<br>Mass: 686 (MH⁺)<br>[α]$_D^{20}$ +38.3° (c = 0.3, methanol) |
| 54 | —CH₂—[4-nitrophenyl] | —(CH₂)₃—[phenyl] | IR*²: 3320, 1753, 1670, 1515, 1350, 1250 cm⁻¹<br>Mass: 670 (MH⁺)<br>[α]$_D^{20}$ +40.0° (c = 0.3, methanol) |
| 55 | —CH(phenyl)₂ | —CH₃ | IR*²: 1740, 1710, 1670, 1510, 1250 cm⁻¹<br>Mass: 597 (MH⁺)<br>[α]$_D^{20}$ +34.3° (c = 0.3, methanol) |

TABLE 7-continued

[Structure: benzothiazepine core with 4-methoxyphenyl-CH, OCH₂COOR² substituent, N-(CH₂)₂N(CH₃)-Q-R⁴ side chain] · fumarate

| Ex. No. | R² | —Q—R⁴ | Physicochemical Properties |
|---|---|---|---|
| 56-(1) | H | —(CH₂)₂—(4-CH₃-phenyl) | IR*²: 3600–2200, 1740, 1670, 1610 cm⁻¹<br>Mass: 535 (MH⁺) |
| 56-(2) | —CH₂—phenyl | —(CH₂)₂—(4-CH₃-phenyl) | IR*²: 3320, 1670, 1630, 1380, 1250 cm⁻¹<br>Mass: 625 (MH⁺)<br>$[\alpha]_D^{20}$ +42.7° (c = 0.3, methanol) |
| 57-(1) | H | —(CH₂)₂—(3,4,5-tri-OCH₃-phenyl) | IR*²: 3600–2200, 1740, 1670, 1610 cm⁻¹<br>Mass: 611 (MH⁺) |
| 57-(2) | —CH₂—phenyl | —(CH₂)₂—(3,4,5-tri-OCH₃-phenyl) | IR*²: 3320, 1670, 1630, 1510 cm⁻¹<br>Mass: 701 (MH⁺)<br>$[\alpha]_D^{20}$ +38.8° (c = 0.08, methanol) |
| 58-(1) | H | —(CH₂)₃—(3,4-di-OCH₃-phenyl) | IR*²: 3600–2200, 1740, 1670, 1610 cm⁻¹<br>Mass: 595 (MH⁺) |
| 58-(2) | —CH₂—phenyl | —(CH₂)₃—(3,4-di-OCH₃-phenyl) | IR*²: 1740, 1670, 1510, 1260 cm⁻¹<br>Mass: 685 (MH⁺)<br>$[\alpha]_D^{20}$ +38.0° (c = 0.3, methanol) |
| 59 | —CH₂CH₂CH₃ | —(CH₂)₂—(3-OCH₃-phenyl) | IR*²: 1745, 1700, 1670, 1607 cm⁻¹<br>Mass: 593 (MH⁺)<br>$[\alpha]_D^{21}$ +66.3° (c = 1.04, methanol) |
| 60 | —CH₂CH(CH₃)₂ | —(CH₂)₂—(3-OCH₃-phenyl) | IR*²: 1745, 1700, 1670, 1640, 1605 cm⁻¹<br>Mass: 607 (MH⁺)<br>$[\alpha]_D^{20}$ +64.8° (c = 1.02, methanol) |

TABLE 7-continued

[Structure: benzothiazepine with substituents: S-CH(4-methoxyphenyl)-CH(OCH₂COOR²)-C(=O)-N, with (CH₂)₂N(CH₃)Q-R⁴ on nitrogen] .fumarate

| Ex. No. | R² | —Q—R⁴ | Physicochemical Properties |
|---|---|---|---|
| 61 | —C(CH₃)₃ | —(CH₂)₂—(3-methoxyphenyl) | IR*²: 1740, 1710, 1670, 1607 cm⁻¹<br>Mass: 607 (MH⁺)<br>$[\alpha]_D^{20}$ +66.9° (c = 0.974, methanol) |
| 62 | —CH(CH₃)₂ | —(CH₂)₂—(3-methoxyphenyl) | IR*²: 1740, 1700, 1670, 1600, 1580, 1510, 1250 cm⁻¹<br>Mass: 593 (MH⁺)<br>$[\alpha]_D^{20}$ +62.5° (c = 0.339, methanol) |
| 63 | —CH₂—phenyl | —(CH₂)₂—(3-methoxyphenyl) | IR*²: 1750, 1700, 1670, 1600, 1580, 1510, 1250 cm⁻¹<br>Mass: 641 (MH⁺)<br>$[\alpha]_D^{20}$ +57.8° (c = 0.287, methanol) |
| 64 | —CH₃ | —(CH₂)₂—(3-methoxyphenyl) | IR*²: 1750, 1700, 1670, 1610, 1580, 1510, ',49 cm⁻¹<br>Mass: 565 (MH⁺)<br>$[\alpha]_D^{20}$ +68.9° (c = 0.268, methanol) |

EXAMPLE 65

To a solution of (+)-cis-2-(4-methoxyphenyl)-3-(ethoxycarbonylmethyl)oxy-5- 2-(dimethylamino)ethyl]-2,3-dihydro-1,5-[benzothiazepin-4(5H)-one (6.55 g) and triethylamine (1.01 g) in toluene (50 ml) is added chloroformic acid trichloromethyl ester (2.97 g) at 0° C. The reaction mixture is stirred at room temperature overnight, and concentrated under reduced pressure. The residue is dissolved in ethyl acetate, washed successively with 10% hydrochloric acid and water, and dried. The solvent is distilled off and the resulting residue is purified by silica gel column chromatography (eluent; ethyl acetate: n-hexane=1:1) to give (+)-cis-2-(4-methoxyphenyl)-3-(ethoxycarbonylmethyl)oxy-5-{2-[N-methyl-N-(chlorocarbonyl)amino]ethyl}-2,3-dihydro-1,5-benzothiazepin-4(5H)-one as oily product. This oily product is refluxed in water (80 ml) and acetonitrile (80 ml) for 1 hour. The reaction mixture is concentrated under reduced pressure, and the residue is dissolved in water. This aqueous solution is basified with aqueous sodium hydrogen carbonate solution and then, extracted with chloroform. The extract is washed, dried, and the solvent is distilled off to give (+)-cis-2-(4-methoxyphenyl)-3-(ethoxycarbonylmethyl)oxy-5-[2-(methylamino)ethyl]-2,3-dihydro-1,5-benzothiazepin-4(5H)-one.

½ Fumarate:
M.p. 167.5°–169.5° C. (decomposed; recrystallized from ethanol/isopropyl ether)
IRν (nujol): 2400, 1735, 1670, 1470, 1375, 1250 cm⁻¹.
$[\alpha]_D^{20}$+66.2° (c=0.280, methanol).

EXAMPLE 66

(+)-cis-2-(4-Methoxyphenyl)-3-(ethoxycarbonylmethyl)oxy-5-{2-[N-methyl-N-[3-(4-methylphenyl)propyl]-amino]ethyl}-2,3-dihydro-1,5-benzothiazepin-4(5H)-one is treated in the same manner as described in Example 65 to give (+)-cis-2-(4-methoxyphenyl)-3-(ethoxycarbonylmethyl)-oxy-5-{2-[3-(4-methylphenyl)-propylamino]ethyl}-2,3-dihydro-1,5-benzothiazepin-4(5H)-one fumarate.

IRν $_{max}^{nujol\ (cm-1)}$: 1740, 1710, 1670, 1510, 1250.
Mass: 563 (MH+), 327.
$[\alpha]_D^{20}$+40.0° (c=0.230, methanol).

EXAMPLES 67–68

(+)-cis-2-(4-Methoxyphenyl)-3-hydroxy-5-[2-(dimethylamino)ethyl]-8-chloro-2,3-dihydro-1,5-benzothiazepin-4(5H)-one or (+)-cis-2-(4-methylphenyl)-3-hydroxy-5-[2-(dimethylamino)ethyl]-8-methyl-2,3-dihydro-1,5-benzothiazepin-4(5H)-one and ethyl bromoacetate are treated in the same manner as described in Examples 1-(2) and 65 to give the compounds shown in Table 8.

TABLE 8

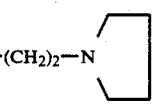

| Ex. No. | X | R¹ | Physicochemical Properties |
|---|---|---|---|
| 67 | Cl | OCH₃ | M.p. 88.4–89.4° C. $[\alpha]_D^{20}$ +69.0° (c = 0.271, methanol) |
| 68 | CH₃ | CH₃ | M.p. 82–83° C. $[\alpha]_D^{20}$ +107.8° (c = 0.574, methanol) |

EXAMPLE 69

A mixture of (+)-cis-2-(4-methoxyphenyl)-3-(ethoxycarbonylmethyl)oxy-5-[2-(methylamino)ethyl]-2,3-dihydro-1,5-benzothiazepin-4(5H)-one (1.0 g), triethylamine (375 mg), cinnamyl bromide (730 mg) and methylene chloride (20 ml) is stirred at room temperature overnight. The reaction mixture is concentrated under reduced pressure, and the resulting residue is purified by silica gel column chromatography (eluent; chloroform: ethanol=20:1) to give (+)-cis-2-(4-methoxyphenyl)-3(ethoxycarbonylmethyl)oxy-5-[2-(N-methyl-N-cinnamylamino)ethyl]-2,3-dihydro-1,5-benzothiazepin-4(5H)-one as oil product.

IRυ (liquid): 1750, 1670, 1610, 1510 cm⁻¹.
Fumarate.hydrate:
$[\alpha]_D^{20}$+56.5° (c=0.390, methanol).

EXAMPLE 70

To a solution of morpholinoethanol (660 mg) in methylene chloride (7 ml) is added anhydrous trifluoromethanesulfonic acid (1.41 g) at room temperature. The mixture is stirred for 2 hours, and thereto is added a mixture of triethylamine (1.01 g), (+)-cis-2-(4-methoxyphenyl)-3-(ethoxycarbonylmethyl)oxy-5-[2-(methylamino)ethyl]-2,3-dihydro-1,5-benzothiazepin-4(5H)-one (2.22 g) and methylene chloride (45 ml). The mixture is stirred at room temperature for two more hours. Chloroform and 5% aqueous sodium hydrogen carbonate solution are added to the mixture. The organic layer is collected, washed and dried. The solvent is distilled off and the resulting residue is purified by silica gel column chromatography (eluent; chloroform: ethanol=15:1) to give (+)-cis-2-(4-methoxyphenyl)-3-(ethoxycarbonylmethyl)oxy-5-{2-[N-methyl-N-(2-morpholinoethyl)amino[ethyl}-2,3-dihydro-1,5-benzothiazepin-4(5H)-one.

Difumarate:
M p. 104°–106° C.
IRυ (nujol): 1720, 1305 cm⁻¹.
Mass: 557 (M+).
$[\alpha]_D^{20}$+45.0° (c=0.3, methanol).

EXAMPLES 71–114

The compounds of the following Tables 9 and 10 are obtained by treating the corresponding starting compounds in the same manner as in Example 70.

TABLE 9

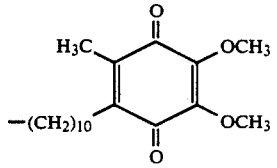

| Ex. No. | —Q—R⁴ | Physicochemical Properties |
|---|---|---|
| 71 | —(CH₂)₂—N⟨ ⟩ (pyrrolidinyl) | Difumarate: IR*²: 2950, 1750, 1675, 1510, 1250 cm⁻¹ Mass: 542 (MH+) $[\alpha]_D^{20}$ +41.7° (c = 0.3, methanol) |
| 72 | —(CH₂)₁₀— (2,5-dimethoxy-3-methyl-1,4-benzoquinonyl) | Fumarate: IR*²: 1670, 1510, 1275 cm⁻¹ Mass: 767 (MH+ + 2) $[\alpha]_D^{20}$ +31.7° (c = 0.3, methanol) |

TABLE 9-continued

[Structure: benzothiazepine core with OCH₃-phenyl, OCH₂COOCH₂CH₃, and (CH₂)₂N(CH₃)Q-R⁴ substituents]

| Ex. No. | —Q—R⁴ | Physicochemical Properties |
|---|---|---|
| 73 | —C(O)— (indol-2-yl, NH) | IR*²: 3280, 1745, 1610, 1250 cm⁻¹<br>Mass: 588 (MH⁺)<br>$[\alpha]_D^{20}$ +50.0° (c = 0.3, methanol) |
| 74 | —CH₂— (2-hydroxyphenyl) | M.p. 90–93° C.<br>IR*²: 3280, 1740, 1610, 1250 cm⁻¹<br>Mass: 551 (MH⁺)<br>$[\alpha]_D^{20}$ +44.0° (c = 0.3, methanol) |
| 75 | —(CH₂)₂—N(piperazine)—N—CH(phenyl)₂ | Trifumarate:<br>IR*²: 1670, 1250 cm⁻¹<br>Mass: 737 (MH⁺)<br>$[\alpha]_D^{20}$ +40.0° (c = 0.3, methanol) |
| 76 | —(CH₂)₂—S—CH₂—phenyl | Fumarate:<br>IR*²: 1705, 1670, 1510, 1250 cm⁻¹<br>Mass: 535 (MH⁺—CH₂SCH₂)<br>$[\alpha]_D^{*}$ +60.0° (c = 0.3, methanol) |
| 77 | —(CH₂)₂—S—(4-CF₃-phenyl) | Fumarate:<br>IR*²: 2690, 1670, 1425, 1280, 1230, 1005, 930 cm⁻¹<br>Mass: 649 (MH⁺)<br>$[\alpha]_D^{20}$ +24.7° (c = 0.3, methanol) |
| 78 | —(CH₂)₂—(5-chlorobenzo[b]thiophen-3-yl) | Fumarate:<br>IR*²: 1700, 1670, 1510, 1250 cm⁻¹<br>Mass: 639 (MH⁺)<br>$[\alpha]_D^{20}$ +59.0° (c = 0.3, methanol) |
| 79 | —(CH₂)₃—O—(4-fluorophenyl) | Fumarate:<br>IR*²: 2900, 1745, 1710, 1675, 1510, 1250, 1210 cm⁻¹<br>$[\alpha]_D^{20}$ +59.0° (c = 0.3, methanol) |
| 80 | —(CH₂)₂—(2,3-dihydrobenzofuran-3-yl) | Fumarate:<br>IR*²: 1745, 1670, 1510, 1280, 1250, 1130, 1030 cm⁻¹<br>$[\alpha]_D^{20}$ +62.0° (c = 0.3, methanol) |
| 81 | —(CH₂)₂—O—(3-methoxyphenyl) | Fumarate:<br>IR*²: 3600–2200, 1740, 1710, 1670, 1610, 1250 cm⁻¹<br>Mass: 595 (MH⁺), 457<br>$[\alpha]_D^{20}$ +59.4° (c = 0.256, methanol) |

TABLE 9-continued

[Structure: benzothiazepine core with H-C(4-methoxyphenyl)-S on one side, -OCH₂COOCH₂CH₃ group, N-C(=O)-(CH₂)₂N(CH₃)-Q-R⁴]

| Ex. No. | —Q—R⁴ | Physicochemical Properties |
|---|---|---|
| 82 | —(CH₂)₂—(4-Cl-phenyl) | Fumarate: IR*²: 3600–2200, 1740, 1700, 1670, 1250 cm⁻¹; Mass: 585, 583 (M⁺); $[\alpha]_D^{20}$ +60.7° (c = 0.244, methanol) |
| 83 | —(CH₂)₂—(3-Cl-phenyl) | Fumarate: IR*²: 3600–2200, 1750, 1710, 1670, 1250 cm⁻¹; Mass: 585, 583 (M⁺); $[\alpha]_D^{20}$ +57.1° (c = 0.392, methanol) |
| 84 | —(CH₂)₂—O—(3,5-dimethoxyphenyl) | Fumarate: IR*²: 3600–2200, 1745, 1700, 1680, 1600, 1250 cm⁻¹; Mass: 625 (MH⁺); $[\alpha]_D^{20}$ +54.9° (c = 0.324, methanol) |
| 85 | —(CH₂)₂—N(CH₃)—phenyl | Fumarate: IR*²: 3600–2200, 1750, 1700, 1670, 1600, 1250 cm⁻¹; Mass: 577 (M⁺); $[\alpha]_D^{20}$ +71.6° (c = 0.339, methanol) |
| 86 | —(CH₂)₂—O—(3,4-methylenedioxyphenyl) | Fumarate: IR*²: 3600–2200, 1740, 1700, 1670, 1640, 1250 cm⁻¹; Mass: 608 (M⁺); $[\alpha]_D^{20}$ +57.5° (c = 0.332, methanol) |
| 87 | —(CH₂)₃—(3,4,5-trimethoxyphenyl) | Fumarate: IR*²: 3400–2200, 1740, 1710, 1670, 1640, 1250 cm⁻¹; Mass: 653 (MH⁺); $[\alpha]_D^{20}$ +55.5° (c = 0.245, methanol) |
| 88 | —(CH₂)₂—(4-NHCOCH₃-phenyl) | Fumarate: IR*²: 3400–2200, 1740, 1670, 1515, 1250 cm⁻¹; Mass: 606 (MH⁺); $[\alpha]_D^{20}$ +58.9° (c = 0.397, methanol) |
| 89 | —(CH₂)₄—(2-thienyl) | Fumarate: IR*²: 3400–2200, 1740, 1700, 1670, 1660, 1250 cm⁻¹; Mass: 583 (MH⁺); $[\alpha]_D^{20}$ +58.9° (c = 0.285, methanol) |

TABLE 9-continued

[Structure shown: benzothiazepine core with 4-methoxyphenyl group, OCH₂COOCH₂CH₃ substituent, and N-(CH₂)₂N(CH₃)-Q-R⁴ side chain]

| Ex. No. | —Q—R⁴ | Physicochemical Properties |
|---|---|---|
| 90 | —(CH₂)₃—[thiophene] | Fumarate:<br>IR*²: 3400–2200, 1740, 1700, 1670, 1650, 1630, 1610, 1250 cm⁻¹<br>Mass: 569 (MH⁺)<br>$[\alpha]_D^{20}$ +61.8° (c = 0.285, methanol) |
| 91 | —(CH₂)₂—[piperidine]—N—COCH₃ | Fumarate:<br>IR*²: 2800–2400, 1740, 1700, 1680, 1640, 1610, 1250 cm⁻¹<br>Mass: 598 (MH⁺)<br>$[\alpha]_D^{20}$ +54.0° (c = 0.285, methanol) |
| 92 | —(CH₂)₂—[phenyl]—N(CH₃)₂ | Fumarate:<br>IR*²: 3400–2200, 1750, 1710, 1670, 1640, 1460, 1250 cm⁻¹<br>Mass: 592 (MH⁺)<br>$[\alpha]_D^{20}$ +46.9° (c = 0.358, methanol) |
| 93 | —(CH₂)₂—NHSO₂—[phenyl]—CH₃ | Fumarate:<br>IR*²: 3400–2800, 1740, 1700, 1675, 1460, 1250 cm⁻¹<br>Mass: 642 (MH⁺)<br>$[\alpha]_D^{20}$ +56.61 (c = 0.431, methanol) |
| 94 | —(CH₂)₂—[phenyl]—NHSO₂—CH₃ | Fumarate:<br>IR*²: 2800–2200, 1740, 1700, 1670, 1460, 1250 cm⁻¹<br>Mass: 642 (MH⁺)<br>$[\alpha]_D^{20}$ +55.8° (c = .319, methanol) |
| 95 | —(CH₂)₂—O—[phenyl]—CN | Fumarate:<br>IR*²: 2800–2200, 2220, 1740, 1700, 1670, 1610, 1460, 1250 cm⁻¹<br>Mass: 590 (MH⁺)<br>$[\alpha]_D^{20}$ +69.8° (c = 0.421, methanol) |
| 96 | —CH₂—CH(OCH₃)—[phenyl] | Fumarate:<br>IR*²: 2800–2200, 1745, 1705, 1670, 1460, 1250 cm⁻¹<br>Mass: 579 (MH⁺)<br>$[\alpha]_D^{20}$ +67.1° (c =0.331, methanol) |
| 97 | —(CH₂)₂—O—[phenyl]—CO₂CH₃ | Fumarate:<br>IR*²: 2800–2200, 1750, 1710, 1670, 1610, 1460, 1250 cm⁻¹<br>Mass: 623 (MH⁺)<br>$[\alpha]_D^{20}$ +63.7° (c = 0.405, methanol) |

TABLE 9-continued

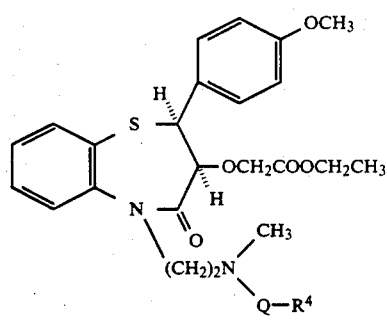

| Ex. No. | —Q—R⁴ | Physicochemical Properties |
|---|---|---|
| 98 | —(CH₂)₂—[furan] | Fumarate:<br>IR*²: 2800–2200, 1740, 1700, 1670, 1460, 1250 cm⁻¹<br>Mass: 539 (MH⁺)<br>$[\alpha]_D^{20}$ +64.7°(c = 0.283, methanol) |
| 99 | —(CH₂)₂—[phenyl-3-CH₃] | Fumarate:<br>Mass: 563 (MH⁺)<br>logout$[\alpha]_D^{20}$ +67.0° (c = 0.693, methanol)<br>Free base:<br>IR*¹: 1750, 1670, 1610, 1510, 1250 cm⁻¹ |
| 100 | —(CH₂)₂—[phenyl-2-CH₃] | Fumarate:<br>Mass: 563 (MH⁺)<br>$[\alpha]_D^{20}$ +69.1° (c = 0.353, methanol)<br>Free base:<br>IR*¹: 1750, 1675, 1610, 1510, 1250 cm⁻¹ |
| 101 | —(CH₂)₂—[phenyl-4-CH(CH₃)₂] | Fumarate:<br>IR*²: 3400–2200, 1750, 1705, 1675, 1460, 1250 cm⁻¹<br>Mass: 591 (MH⁺)<br>$[\alpha]_D^{20}$ +65.0° (c = 0.400, methanol) |
| 102 | —(CH₂)₂—[phenyl-4-CH₂CH₃] | Fumarate:<br>IR*²: 3400–2200, 1750, 1705, 1675, 1460, 1250 cm⁻¹<br>Mass: 577 (MH⁺)<br>$[\alpha]_D^{20}$ +66.4° (c = 0.545, methanol) |
| 103 | —(CH₂)₂—[phenyl-4-OCH₂CH₃] | Fumarate:<br>IR*²: 3000–2200, 1750, 1705, 1675, 1455, 1250 cm⁻¹<br>Mass: 593 (MH⁺)<br>$[\alpha]_D^{20}$ +61.5° (c = 0.566, methanol) |
| 104 | —(CH₂)₂—[phenyl-2,3-diOCH₃] | Fumarate:<br>IR*²: 3000–2200, 1750, 1700, 1465, 1250 cm⁻¹<br>Mass: 609 (MH⁺)<br>$[\alpha]_D^{20}$ +64.2° (c = 0.530, methanol) |
| 105 | —(CH₂)₂—[phenyl-2,5-diOCH₃] | Fumarate:<br>IR*²: 3000–2200, 1745, 1700, 1675, 1470, 1250 cm⁻¹<br>Mass: 609 (MH⁺)<br>$[\alpha]_D^{20}$ +61.3° (c = 0.630, methanol) |

TABLE 9-continued

[Structure: benzothiazepine core with 4-methoxyphenyl, OCH₂COOCH₂CH₃, and (CH₂)₂N(CH₃)(Q-R⁴) substituents]

| Ex. No. | —Q—R⁴ | Physicochemical Properties |
|---|---|---|
| 106 | —(CH₂)₂—(2,4-dimethylphenyl) | Fumarate: IR*[2]: 3000–2200, 1750, 1700, 1670, 1460, 1250 cm$^{-1}$ <br> Mass: 577 (MH$^+$) <br> $[\alpha]_D^{20}$ +63.2° (c = 0.481, methanol) |
| 107 | —(CH₂)₂—(2,4,5-trimethylphenyl) | Fumarate: IR*[2]: 3000–2200, 1740, 1700, 1680, 1640 cm$^{-1}$ <br> Mass: 591 (MH$^+$) <br> $[\alpha]_D^{20}$ +74.7° (c = 0.342, methanol) |
| 108 | —(CH₂)₂—(2,5-dimethylphenyl) | Fumarate: IR*[2]: 3000–2200, 1740, 1700, 1680, 1640 cm$^{-1}$ <br> Mass: 577 (MH$^+$) <br> $[\alpha]_D^{30}$ +69.1° (c = 0.337, methanol) |
| 109 | —(CH₂)₂—(3,4-dimethylphenyl) | Fumarate: IR*[2]: 3000–2200, 1740, 1700, 1670, 1640 cm$^{-1}$ <br> Mass: 577 (MH$^+$) <br> $[\alpha]_D^{20}$ +69.5° (c = 0.334, methanol) |
| 110 | —(CH₂)₂—(2,3,4-trimethoxyphenyl) | Fumarate: IR*[2]: 3000–2200, 1740, 1700, 1680, 1640 cm$^{-1}$ <br> Mass: 639 (MH$^+$) <br> $[\alpha]_D^{20}$ +58.0° (c = 0.345, methanol) |
| 111 | —(CH₂)₂—(2,5-dimethoxyphenyl) | Fumarate: IR*[2]: 3000–2200, 1740, 1700, 1670, 1640 cm$^{-1}$ <br> Mass: 609 (MH$^+$) <br> $[\alpha]_D^{20}$ +59.4° (c = 0.288, methanol) |
| 112 | —(CH₂)₂—(2,5-dimethoxyphenyl) | Fumarate: IR*[2]: 3000–2200, 1740, 1700, 1680, 1600 cm$^{-1}$ <br> Mass: 608 (M$^+$) <br> $[\alpha]_D^{20}$ + 47.0° (c = 0.383, methanol) |

TABLE 10

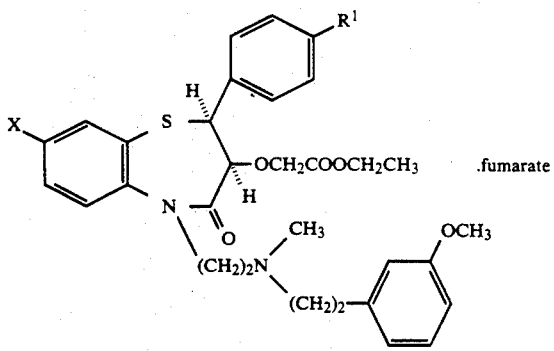

| Ex. No. | X | R¹ | Physicochemical Properties |
|---|---|---|---|
| 113 | Cl | OCH₃ | IR*²: 1750, 1700, 1680, 1610 1510, 1260 cm⁻¹ Mass: 613 (M⁺) [α]$_D^{20}$ +38.8° (c = 0.847, methanol) |
| 114 | CH₃ | CH₃ | IR*²: 1750, 1700, 1670, 1650, 1640, 1260 cm⁻¹ Mass: 576 (M⁺) [α]$_D^{20}$ +60.7° (c = 0.685, methanol) |

EXAMPLE 115

(1) To a mixture of a solution of (+)-cis-2-(4-methoxyphenyl)-3-(ethoxycarbonylmethyl)oxy-5-(2-methylaminoethyl)-2,3-dihydro-1,5-benzothiazepin-4(5H)-one (579 mg) in chloroform (7 ml) and 10% aqueous sodium hydrogen carbonate solution (10 ml) is added a solution of thiophen-2-acetyl chloride (213 mg) in chloroform (5 ml) with stirring. The mixture is stirred at room temperature for 3 hours. After the completion of the reaction, the chloroform layer is collected, washed with water and dried. The solvent is distilled off to give (+)-cis-2-(4-methoxyphenyl)-3-(ethoxycarbonylmethyl)oxy-5-{2-[N-methyl-N-(2-thienylacetyl)amino]-ethyl}-2,3-dihydro-1,5-benzothiazepin-4(5H)-one (800 mg).

(2) This product (800 mg) is dissolved in tetrahydrofuran (60 ml) and thereto is added a 2 M solution of borane-dimethylsulfide in tetrahydrofuran (1.44 ml). The mixture is stirred at room temperature for two days, and thereto are added successively methanol (10 ml) and oxalic acid (300 mg), and the mixture is refluxed for 3 hours. The reaction mixture is concentrated under reduced pressure and to the resulting residue are added ethyl acetate and 5% aqueous sodium hydrogen carbonate solution. The mixture is extracted with ethyl acetate, and the extract is washed and dried. The solvent is distilled off and the resulting residue is purified by silica gel column chromatography (eluent; chloroform: ethanol=15:1) to give (+)-cis-2-( 4-methoxyphenyl)-3-(ethoxycarbonylmethyl)oxy-5-}2-[N-methyl-N-[2-(2-thienyl)ethyl]amino]ethyl}-2,3-dihydro-1,5-benzothiazepin-4(5H)-one as oily product.

Fumarate:
The physicochemical properties of this product are the same as those of the desired compound of Example 10-(2).

EXAMPLE 116

A mixture of a solution of (±)-cis-2-(4-methoxyphenyl)-3-(benzyloxycarbonylmethyl)oxy-5-[2-(dimethylamino)ethyl]-2,3-dihydro-1,5-benzothiazepin-4(5H)-one (880 mg) in a mixed solvent of 10% aqueous sodium hydroxide solution (2 ml), water (15 ml) and ethanol (15 ml) is stirred at 50° C. for 30 minutes. After the completion of the reaction, ethanol is distilled off under reduced pressure. The aqueous layer is washed with ethyl acetate and acidified with acetic acid under ice-cooling, and then, saturated with ammonium sulfate. The precipitated crystal is collected by filtration, washed with water and dried to give (±)-cis-2-(4-methoxyphenyl)-3-(carboxymethyl)oxy-5-[2-(dimethylamino)-ethyl]-2,3-dihydro-1,5-benzothiazepin-4(5H)-one (230 mg), m.p. 184°–188° C. (decomposed).

What is claimed is:

1. A 1,5-benzothiazepine compound of the formula:

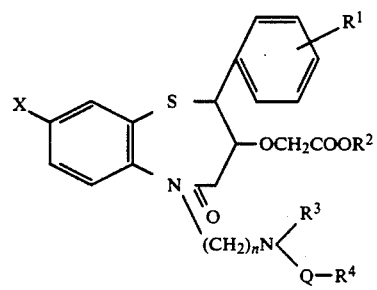

wherein
X is a hydrogen atom, a halogen atom or a lower alkyl group,
R¹ is a lower alkyl group or a lower alkoxy group,
R² is a hydrogen atom, a lower alkyl group a phenyl-lower alkyl group or a phenyl-lower alkyl group substituted by a nitro group,
R³ is a lower alkyl group,
Q is an alkylene group,
R⁴ is a phenyl group, a phenyl group substituted by 1 to 3 substituents selected from the group consisting of lower alkyl and lower alkoxy, or R⁴ is a thienyl group, and
n is 2; or
a pharmaceutically acceptable salt thereof.

2. The compound according to claim 1, wherein X is a hydrogen atom and R¹ is a lower alkoxy group.

3. The compound according to claim 2, wherein R² is a hydrogen atom.

4. The compound according to claim 2, wherein R² is a lower alkyl group, a phenyl-lower alkyl group, or a phenyl-lower alkyl group substituted by a nitro group.

5. The compound according to claim 2, wherein R² is a lower alkyl group, R⁴ is a phenyl group or a phenyl group substituted by a lower alkoxy group.

6. The compound according to claim 5, wherein R¹ is a methoxy group, R² is a ethyl group, R³ is a methyl group, Q is an ethylene group or a trimethylene group, R⁴ is a phenyl group or a phenyl group substituted by a methoxy group.

7. A pharmaceutical composition, which comprises: a calcium antagonistic effective amount of a compound as set forth in claim 1, 2, 4, 5 or 6, in admixture with a pharmaceutically acceptable carrier or diluent therefor.

8. A method of producing a hypotensive effect in a warm-blooded animal which comprises administering to said warm-blooded animal a hypotensive effective amount of a compound as recited in claim 1, 2, 4, 5 or 6.

9. A method of producing a cerebral vasodilating effect in a warm-blooded animal which comprises administering to said warm-blooded animal a cerebral vasodilating effective amount of a compound as recited in claim 1, 2, 4, 5 or 6.

10. A method of producing a coronary vasodilating effect in a warm-blooded animal, which comprises administering to said warm-blooded animal a coronary vasodilating effective amount of a compound as recited in claim 1, 2, 4, 5 or 6.

11. A method of producing an antiarrhythmic effect in a warm-blooded animal, which comprises administering to said warm-blooded animal an antiarrhythmic effect amount of a compound as recited in claim 1, 2, 4, 5 or 6.

* * * * *